United States Patent
Gill et al.

(10) Patent No.: US 6,291,667 B1
(45) Date of Patent: Sep. 18, 2001

(54) METHOD AND COMPOSITION FOR TREATMENT OF KAPOSI'S SARCOMA

(76) Inventors: Parkash S. Gill, 29420 Cresthaven Ct., Agoura, CA (US) 91301; Rizwan Masood, 8225 Garbaldi Ave., San Gabriel, CA (US) 91775

( * ) Notice: Subject to any disclaimer, the term of this patent is extended or adjusted under 35 U.S.C. 154(b) by 0 days.

(21) Appl. No.: 09/016,541

(22) Filed: Jan. 30, 1998

Related U.S. Application Data

(60) Provisional application No. 60/037,004, filed on Jan. 31, 1997.

(51) Int. Cl.[7] ............................. C07H 21/04; C07H 21/02
(52) U.S. Cl. ...................... 536/24.5; 536/23.1; 536/24.3
(58) Field of Search .................... 514/44, 2; 536/23.1, 536/24.3, 24.5

(56) References Cited

U.S. PATENT DOCUMENTS

| | | | |
|---|---|---|---|
| 5,264,423 | 11/1993 | Cohen et al. | 514/44 |
| 5,591,721 | 1/1997 | Agrawal et al. | 514/44 |
| 5,639,736 | 6/1997 | Robinson | 514/44 |
| 5,639,872 | 6/1997 | Robinson | 536/24.5 |
| 5,641,756 | 6/1997 | Robinson | 514/44 |
| 5,652,355 | 7/1997 | Metelev et al. | 514/44 |
| 5,652,356 | 7/1997 | Agrawal | 536/24.5 |
| 5,661,135 | 8/1997 | Robinson | 514/44 |
| 5,710,136 | 1/1998 | Robinson et al. | 514/44 |
| 5,859,228 * | 1/1999 | Janjic et al. | 536/24.3 |

OTHER PUBLICATIONS

Stein. Nature Biotechnology. vol. 17, p. 751, Aug. 1999.*
Genbank database search, accession M32977, Apr. 1993.*
Matsubara et al. Arthritis & Rheumatism, 39, S131, Oct. 1996.*
Mu et al. Japan. J. Cancer Res. 87, 963–71, Sep. 1996.*
Agrawal, S. et al. "Mixed–Backbone Oligonucleotides As Second Generation Antisense Oligonucleotides: In Vitro and In Vivo Studies," (1997) *Proc Natl Acad Sci U S A* 94, 2620–5.
Aguayo,A. etal., "Cellular Vascular Endothelial Growth Factor Is A Predictor of Outcome In Patients With Acute Myeloid Leukemia" (1999) *Blood* 94, 3717–21.
Barleon, B. et al., "Migration of Human Monocytes in Response to Vascular Endothelial Growth Factor (VEGF) Is Mediated Via the VEGF Receptor flt–1," (1996) *Blood* 87, 3336–43.
Benjamin, L. E. & Keshet, E. "Conditional Switching of Vascular Endothelial Growth Factor (VEGF) Expression In Tumors: Induction of Endothelial Cell Shedding and Regression of Hemangioblastoma–Like Vessels by VEGF Withdrawal", (1997) *Proc Natl Acad Sci U S A* 94, 8761–6.
Benjamin, L. E. et al., "Selective Ablation of Immature Blood Vessels in Established Human Tumors Follows Vascular Endothelial Growth Factor Withdrawal" (1999) *J Clin Invest* 103, 159–65.

Chan, A. S. et al., "Expression of Vascular Endothelial Growth Factor and Its Receptors in the Anaplastic Progression of Astrocytoma, Oligodendroglioma, and Ependymoma", (1998) *AmJ Surg Pathol* 22, 816–26.
Charnock–Jones, D. S. et al., "Vascular Endothelial Growth Factor Receptor Localization and Activation in Human Trophoblast and Choriocarcinoma Cells" (1994) *Biol Reprod* 51, 524–30.
Clauss, M. et al., "The Vascular Endothelial Growth Factor Receptor Flt–1 Mediates Biological Activities", (1996) *J Biol Chem* 271, 17629–34.
Crew, J.P. et al., "Vascular Endothelial Growth Factor Is a Predictor of Relapse and Stage Progression in Superficial Bladder Cancer", (1997) *Cancer Res* 57, 5281–5.
De Vries, C. et al., "The fms–Like Tyrosine Kinase, a Receptor for Vascular Endothelial Growth Factor", (1992) *Science* 255, 989–91.
Dias, S. et al., "Expression of VEGF And Its Receptor for VEGFR–2 By Human Leukemia Cell Generates an Autocrine Loop that Mediates Cell Growth and Migration", (2000) in *Proc American Assoc Cancer Res*, 41:792.
Dvorak, H. F. ,et al., "Vascular Permeability Factor/Vascular Endothelial Growth Factor, Microvascular Hyperpermeability, and Angiogenesis", (1995) *Am J Pathol* 146, 1029–39.
El–Assal, O. N. et al., Clinical Significance of Microvessel Density and Vascular Endothelial Growth Factor Expression in Hepatocellular Carcinoma and Surrounding Liver: Possible Involvement of Vascular Endothelial Growth Factor in the Angiogenesis of Cirrhotic Liver (1998) *Hepatology* 27, 1554–62.
Ferrara et al., "Purification and Cloning of Vascular Endothelial Growth Factor Secreted by Pituitary Folliculostellate Cells" (1991) *Methods Enzymol* 198:391–405.
Fidler, I. J. & Ellis, L. M. "The Implications of Angiogenesis for the Biology and Therapy of Cancer Metastasis", (1994) *Cell* 79, 185–8.

(List continued on next page.)

Primary Examiner—Remy Yucel
Assistant Examiner—Lisa Gansheroff
(74) Attorney, Agent, or Firm—McCutchen, Doyle, Brown & Enersen

(57) ABSTRACT

A novel method of treating Kaposi's sarcoma (KS) in patients, by administration of an effective amount of VEGF antagonist/s. VEGF antagonists are capable of inhibiting the growth of KS cells in culture by inhibiting the production of VEGF, or by interfering with the binding of VEGF to its cognate receptors or interfere with the biological effects of VEGF. The VEGF antagonist may be administered to KS patients topically, orally, or parentally. Other VEGF antagonist such as VEGF antibodies, VEGF receptor antibodies, soluble forms of VEGF receptors that bind VEGF away from the cells, or agents that inhibit the signal of VEGF into the cell such as protein kinase inhibitors etc. can also be used. The novel antisense oligonucleotides (Veglin-1 and Veglin-3) may also be used to inhibit VEGF and thus new blood vessel formation in diseases such as tumors, proliferative retinopathy, or collagen vascular diseases such as rheumatoid arthritis, and skin diseases such as pemphigus and psoriasis. The KS cell lines also allow-the screening of other VEGF inhibitors.

12 Claims, 13 Drawing Sheets

OTHER PUBLICATIONS

Fine, B. A. et al., "VEGF, flt–1, and KDR/flk–1 as Prognostic Indicators in Endometrial Carcinoma" (2000) *Gynecol Oncol 76*, 33–9.

Maeda, K. et al., "Vascular Endothelial Growth Factor Expression in Preoperative Biopsy Specimens Correlates with Disease Recurrence in Patients with Early Gastric Carcinoma", (1999) *Cancer 86*, 566–71.

Masood R et al (1997) "Vascular endothelial growth factor/vascular permeability factor is an autocrine growth factor for AIDS–Kaposi sarcoma." *Proc. Natl. Acad. Sci. USA* 94:979–84.

Moriyama, M. et al., "Immunohisochemical Study of Tumour Angiogenesis in Oral Squamous Cell Carcinoma", (1997) *Oral Oncol 33*, 369–74.

Paradis, V. et al., "Expression of Vascular Endothelial Growth Factor in Renal Cell Carcinomas", (2000) *Virchows Arch 436*, 351–6.

Plate, K. H. "Control of Tumour Growth Via Inhibition of Tumor Angiogenesis", (1998) *Adv Exp Med Biol 451*, 57–61.

Senger, D. R., et al., "Vascular Permeability Factor (VPF, VEGF) in Tumor Biology" (1993) *Cancer Metastasis Rev*12, 303–24.

Smith, B. D. et al., "Prognostic Significance of Vascular Endothelial Growth Factor Protein Levels in Oral and Oropharyngeal Squamous Cell Carcinoma" (2000) *J Clin Oncol* 18, 2046–52.

Soker, S. et al., "Neuropilin–1 Is Expressed by Endothelial and Tumor Cells as an Isoform–Specific Receptor for Vascular Endothelial Growth Factor", (1998) *Cell 92*, 735–45.

Takahashi, T. & Shibuya, M. "The 230 kDa Mature Form of KDR/Flk–1 (VEGF Receptor–2) Activates the PLC–y Pathway and Partially Induces Mitotic Signals in NIH3T3 Fibroblasts", (1997) *Oncogene*14, 2079–89.

Terman, B. I. et al., "Identification of the KDR Tyrosine Kinase as a Receptor For Vascular Endothelial Cell Growth Factor", (1992) *Biochem Biophys Res Commun* 187, 1579–86.

Tischer et al "The Human Gene for Vascular Endothelial Growth Factor", (1991) *J. Biol Chem* 266:11947–540.

Waltenberger, J. et al., "Different Signal Transduction Properties of KDR and Flt1, Two Receptors for Vascular Endothelial Growth Factor", (1994) *J Biol Chem* 269, 26988–95.

Wang, D. et al., "Homeostatic Modulation of Cell Surface KDR and Flt 1 Expression and Expression of the Vascular Endothelial Cell Growth Factor (VEGF) Receptor mRNAs by VEGF", (2000) *J Biol Chem* 275, 15905–15911.

Yamamoto S. et al., "Expression of Vascular Endothelial Growth Factor (VEGF) in Epithelial Ovarian Neoplasms: Correlation With Clinicopathology and Patient Survival, and Analysis of Serum VEGF Levels", (1997) *Br J Cancer*, 76(9): 1221–7.

Yukita, A. et al., "Suppression of Ascites Formation and Re–Accumulation Associated With Human Ovarian Cancer by an Anti–VPF Monoclonal Antibody in Vivo", (2000) *Anticancer Res* 20, 155–60.

\* cited by examiner

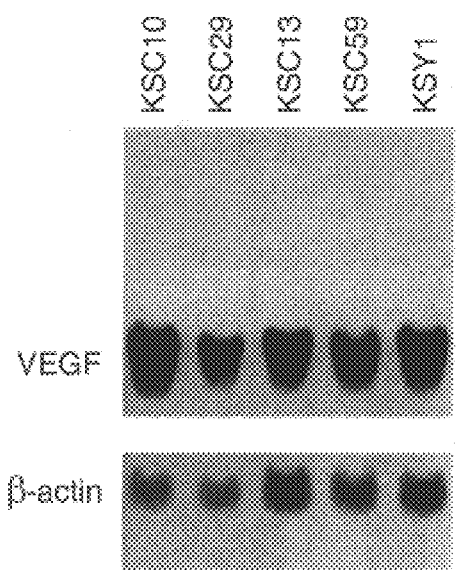
FIG._1A
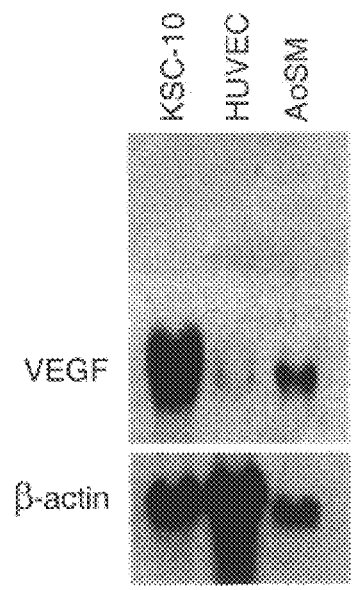
FIG._1B
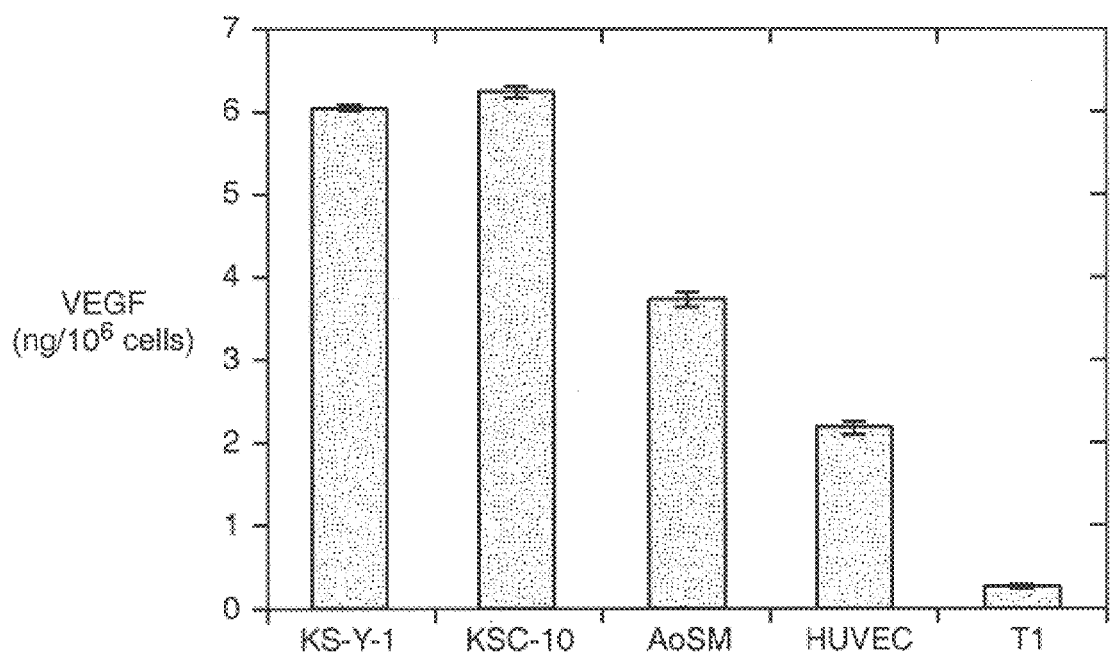
FIG._1C

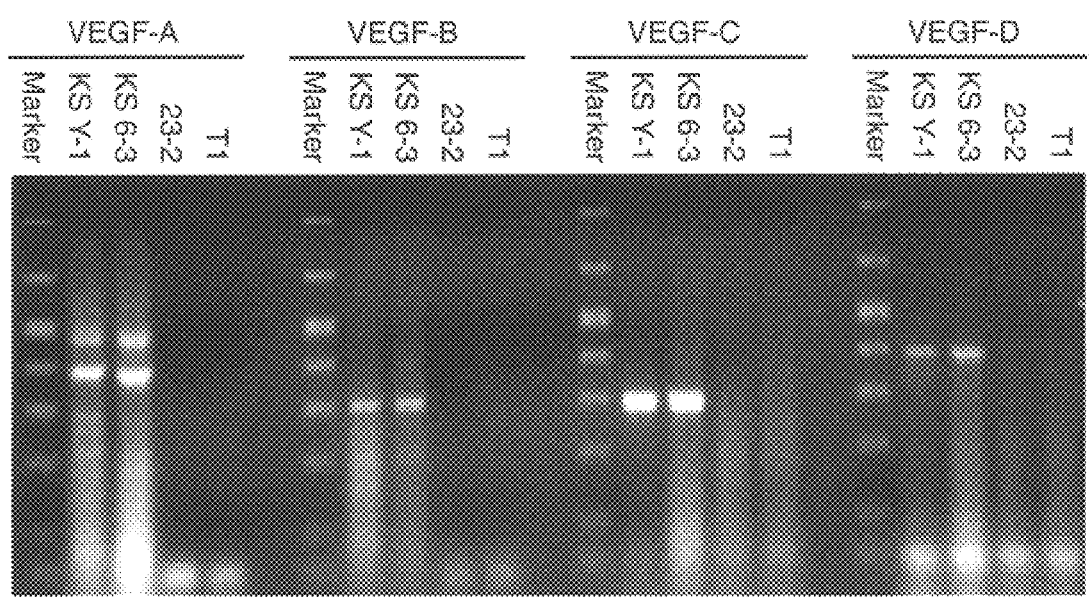
FIG._2

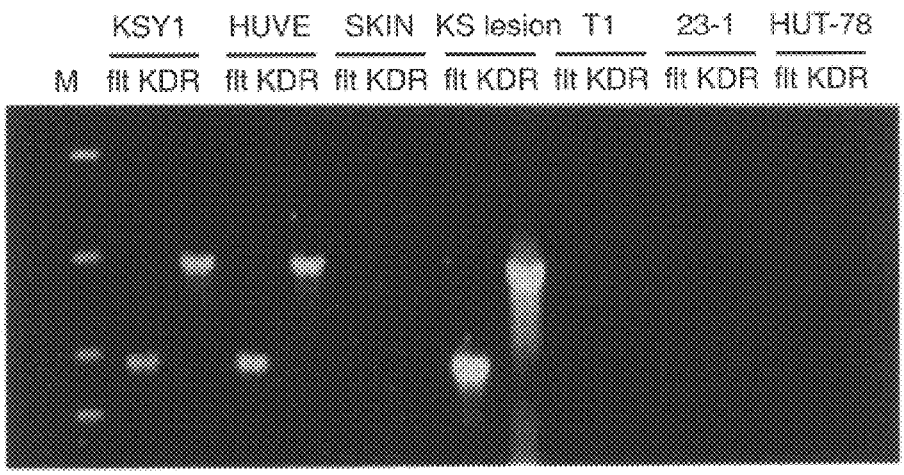
FIG._3A
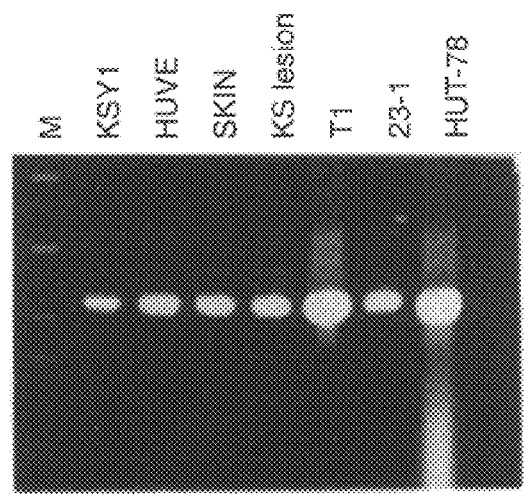
FIG._3B
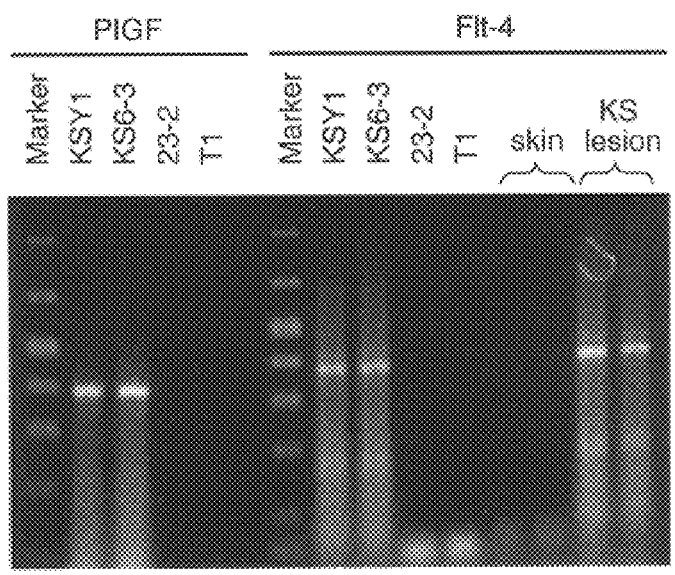
FIG._4

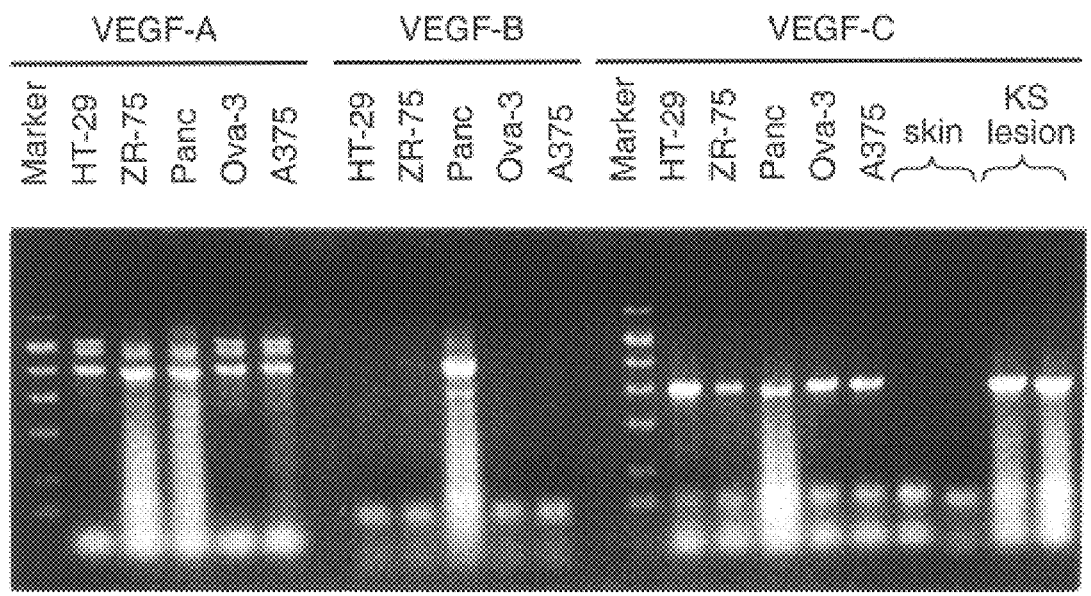
FIG._5A
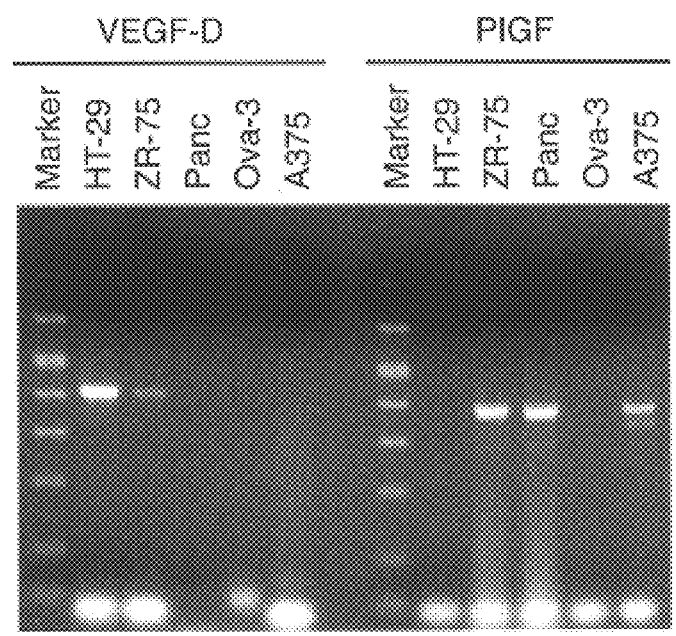
FIG._5B

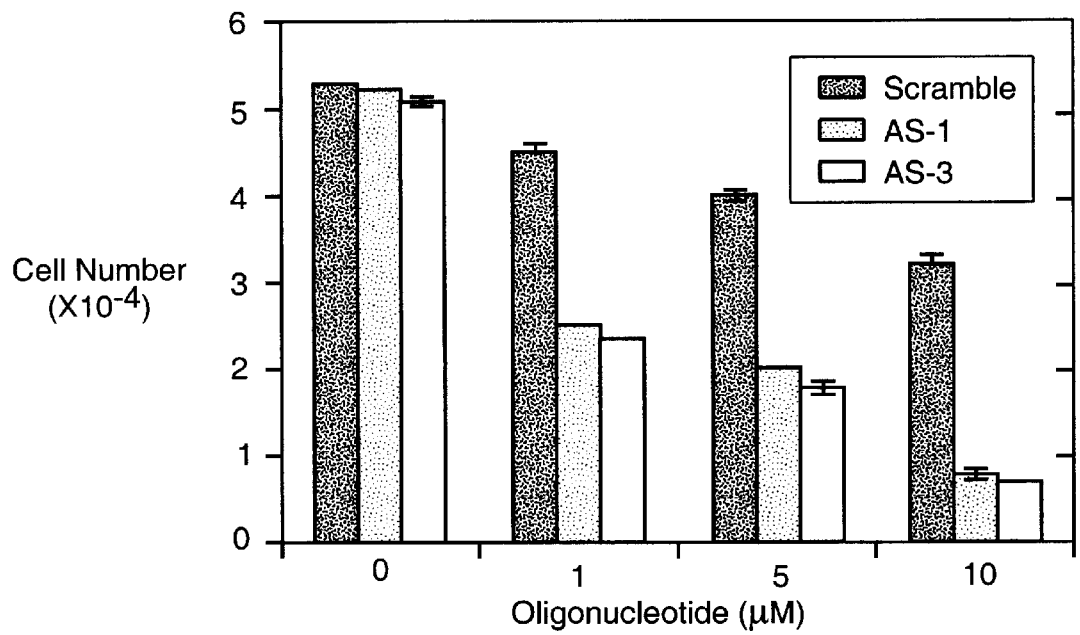
FIG._6A
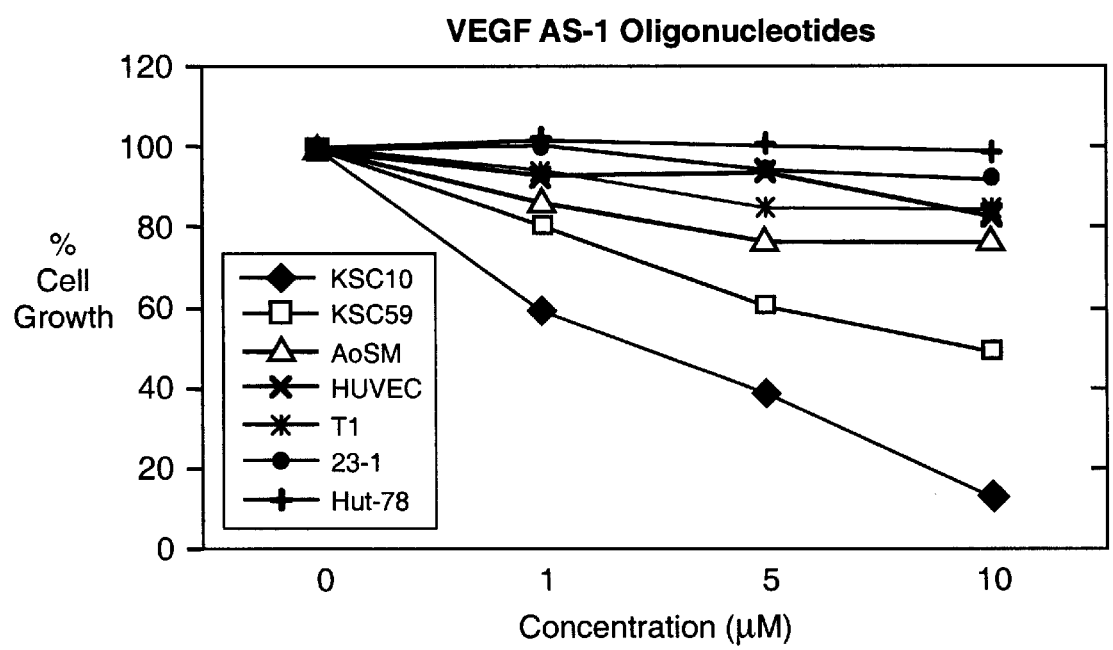
FIG._6B

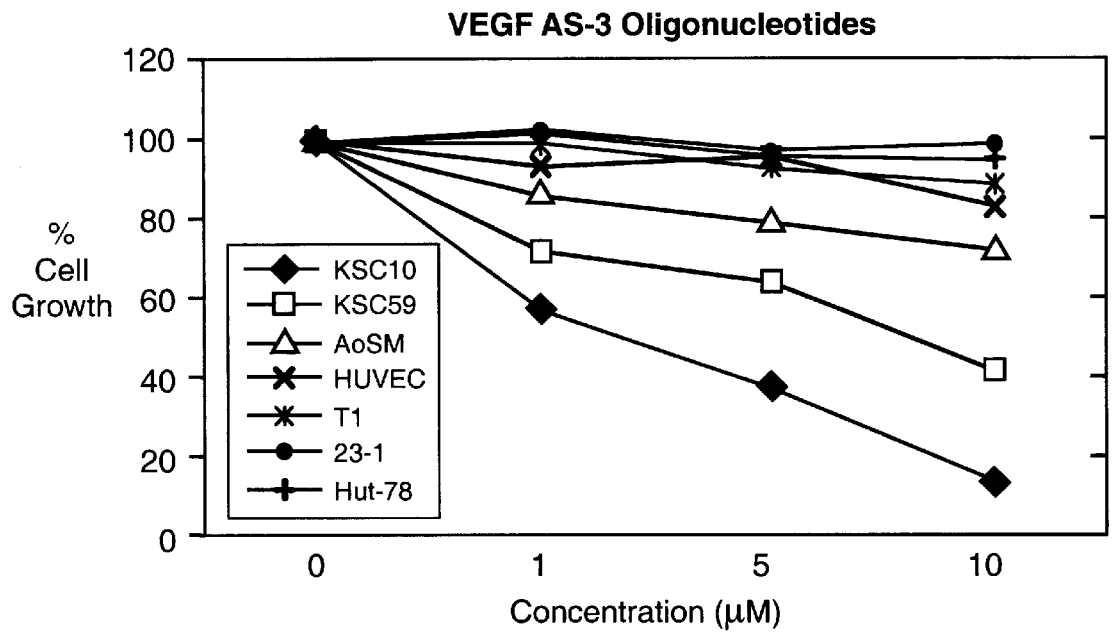
FIG._6C
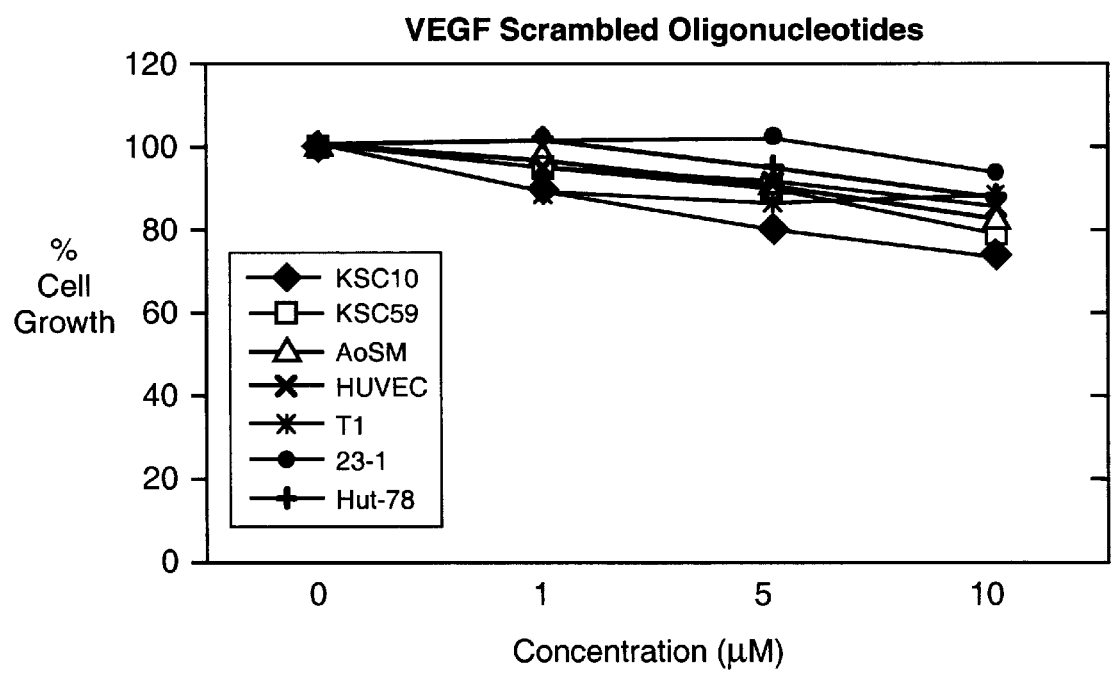
FIG._6D

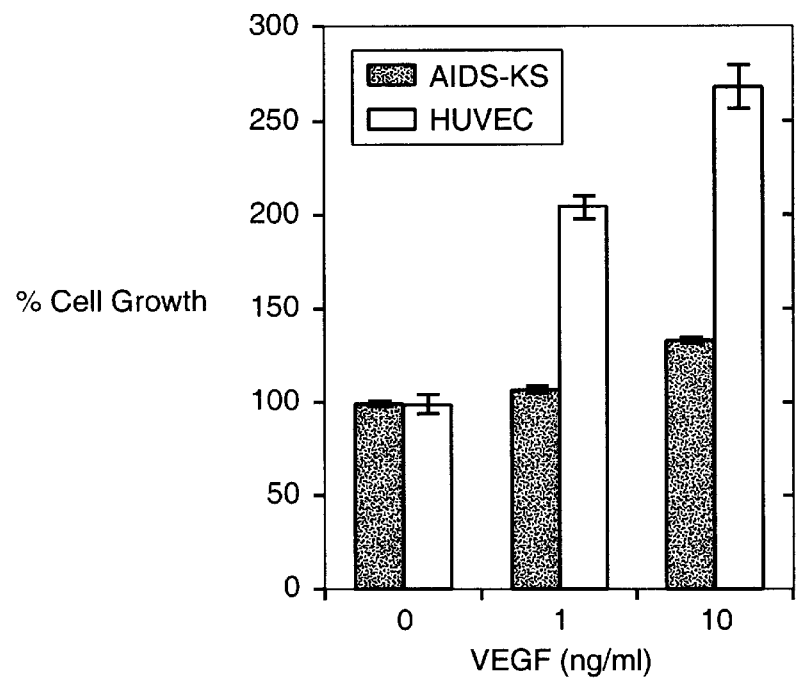
FIG._6E
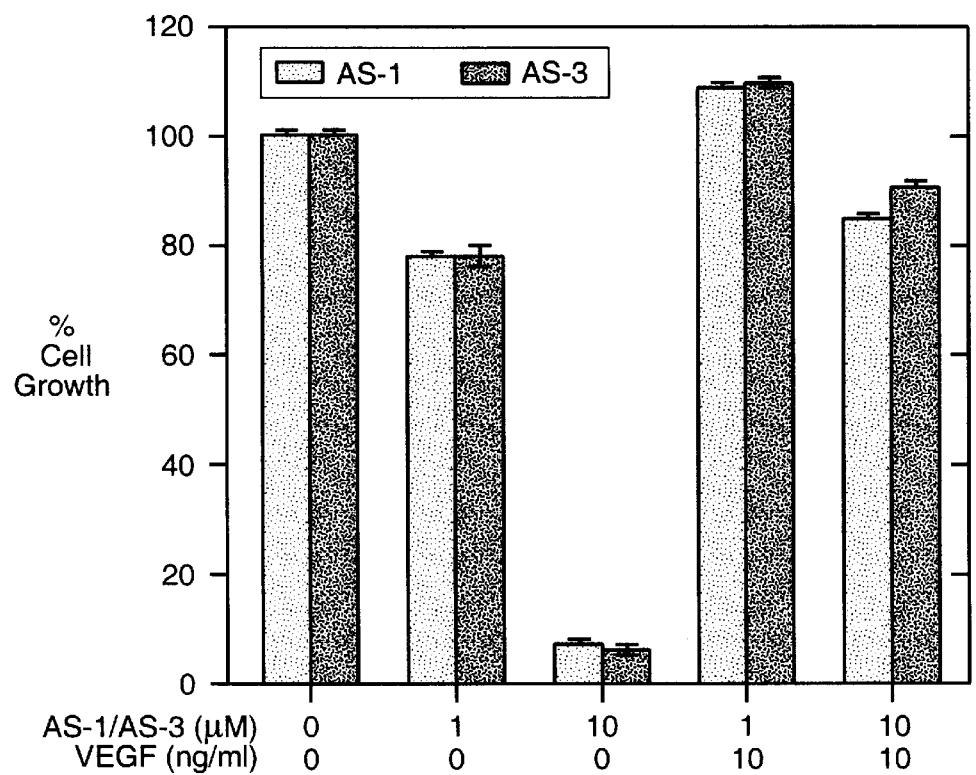
FIG._6F

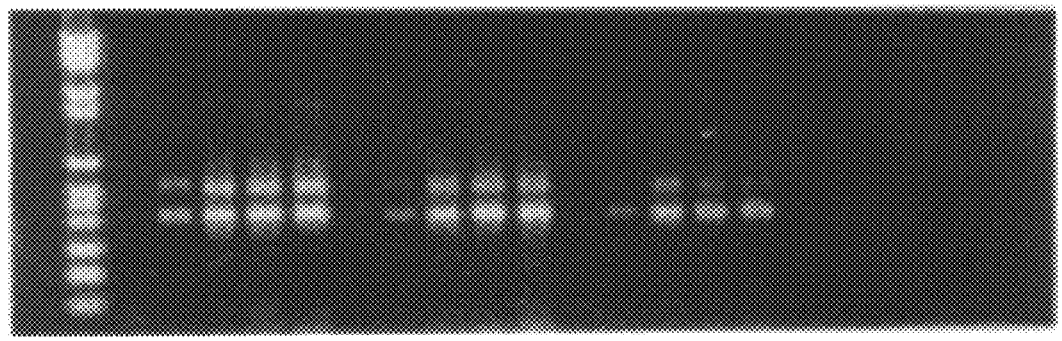
FIG._7A
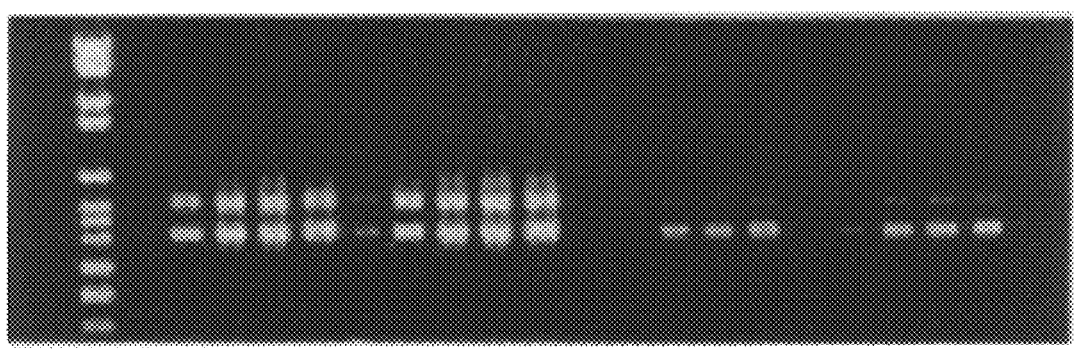
FIG._7B
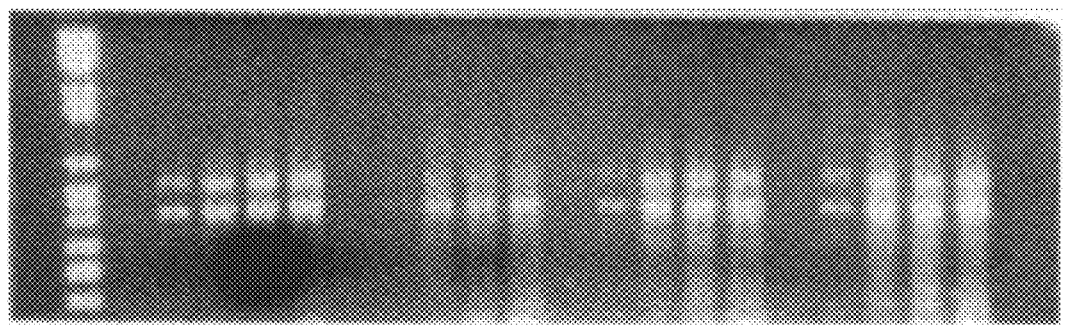
FIG._7C

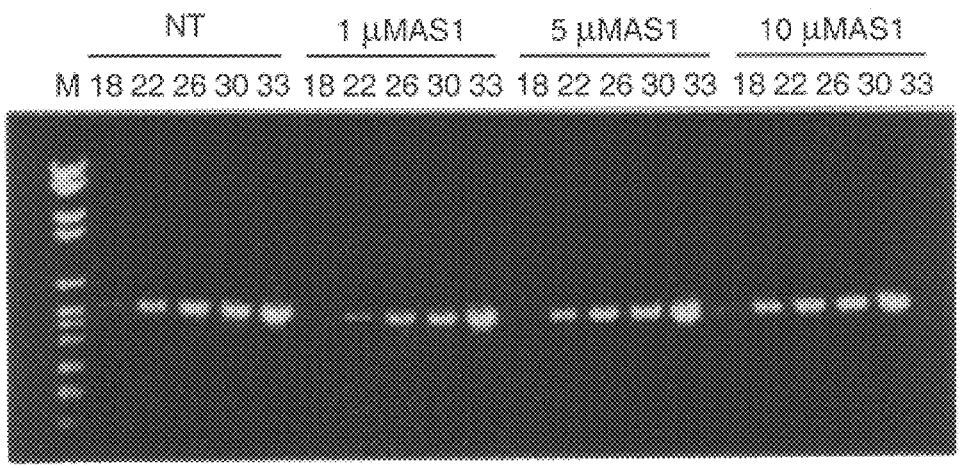
FIG._7D
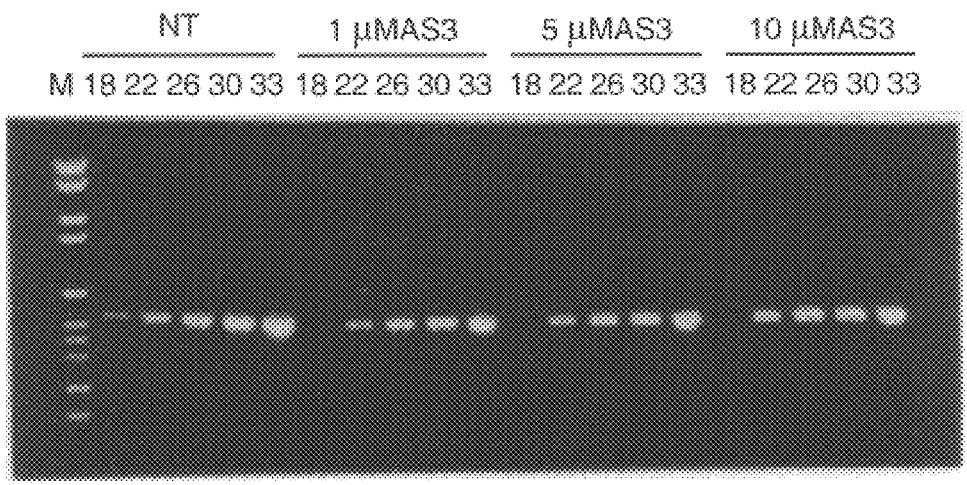
FIG._7E
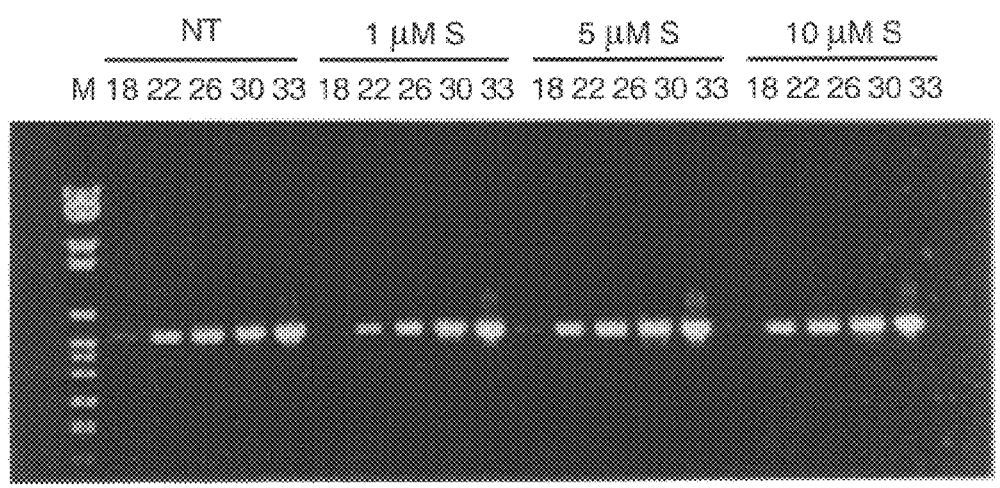
FIG._7F

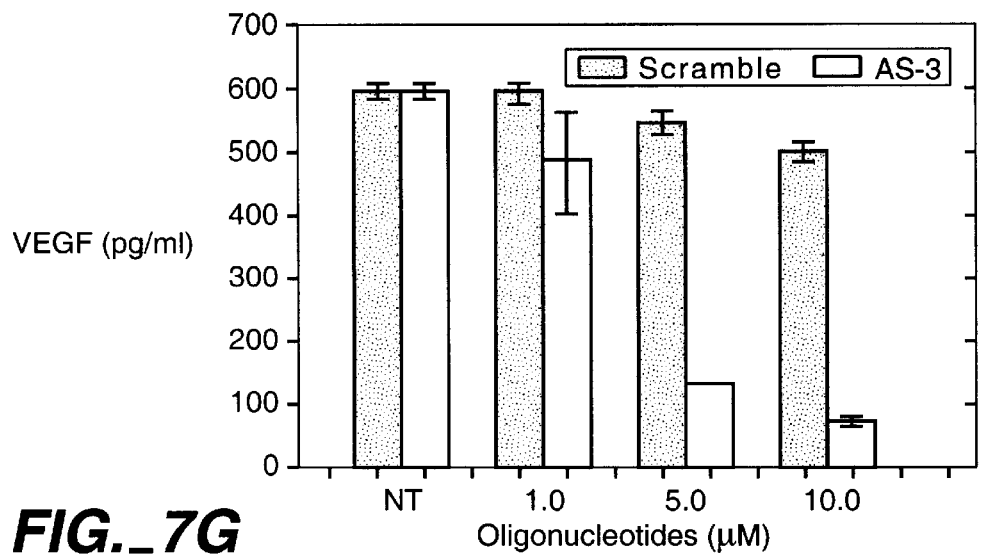
FIG._7G
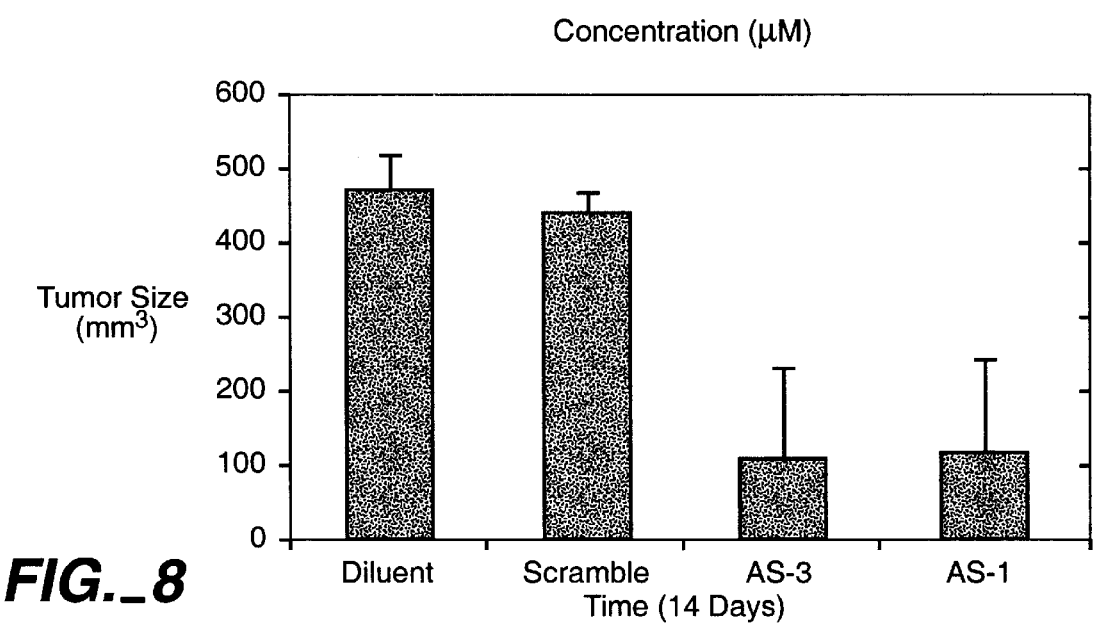
FIG._8

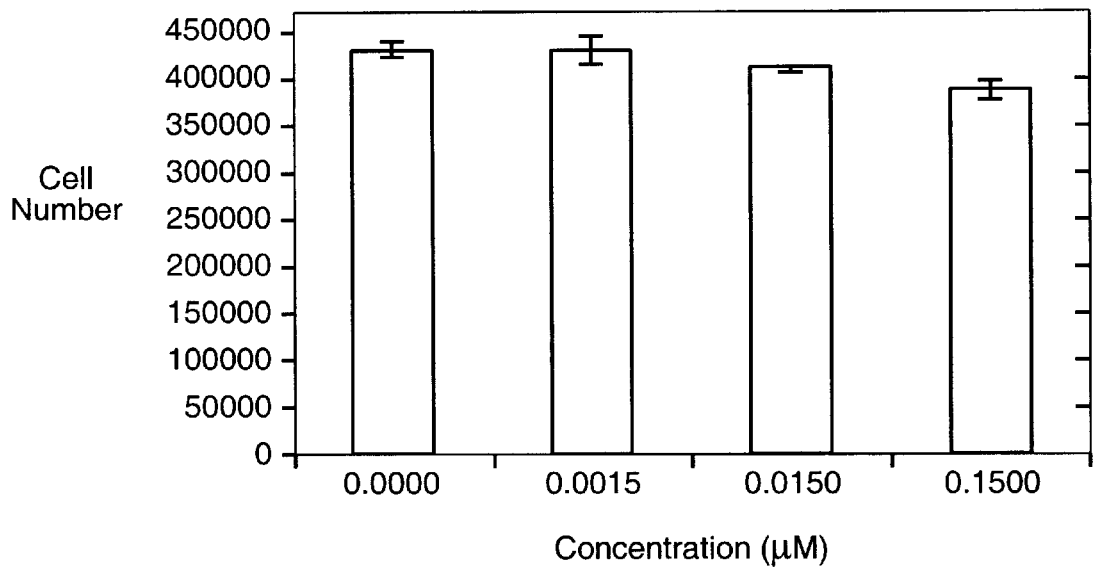
FIG._9A
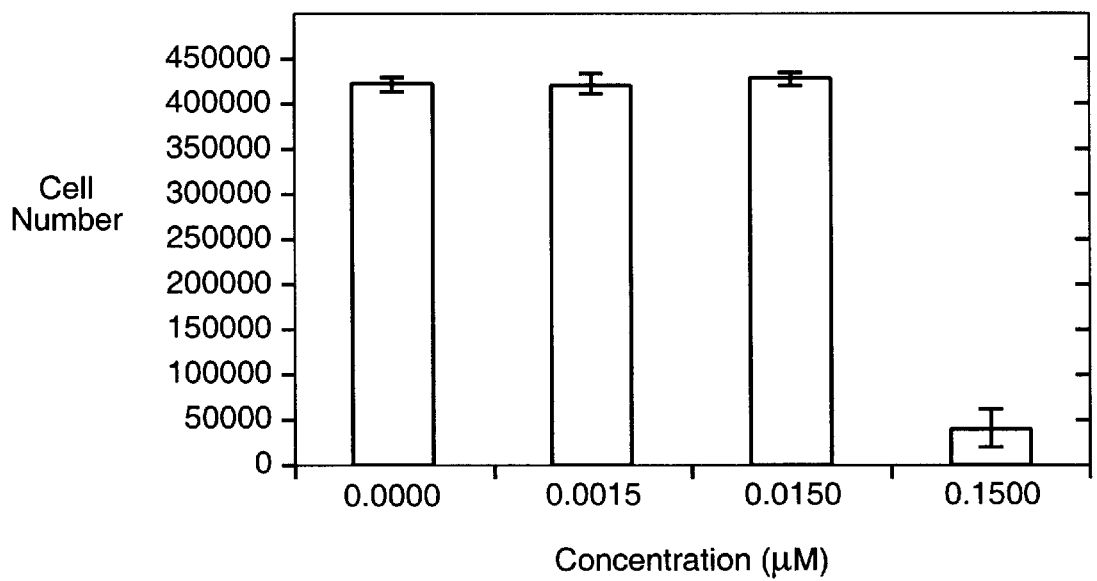
FIG._9B

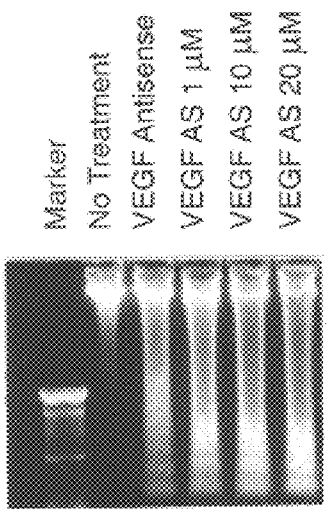
FIG._10A
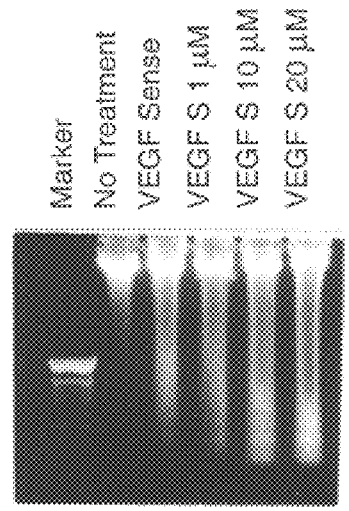
FIG._10B
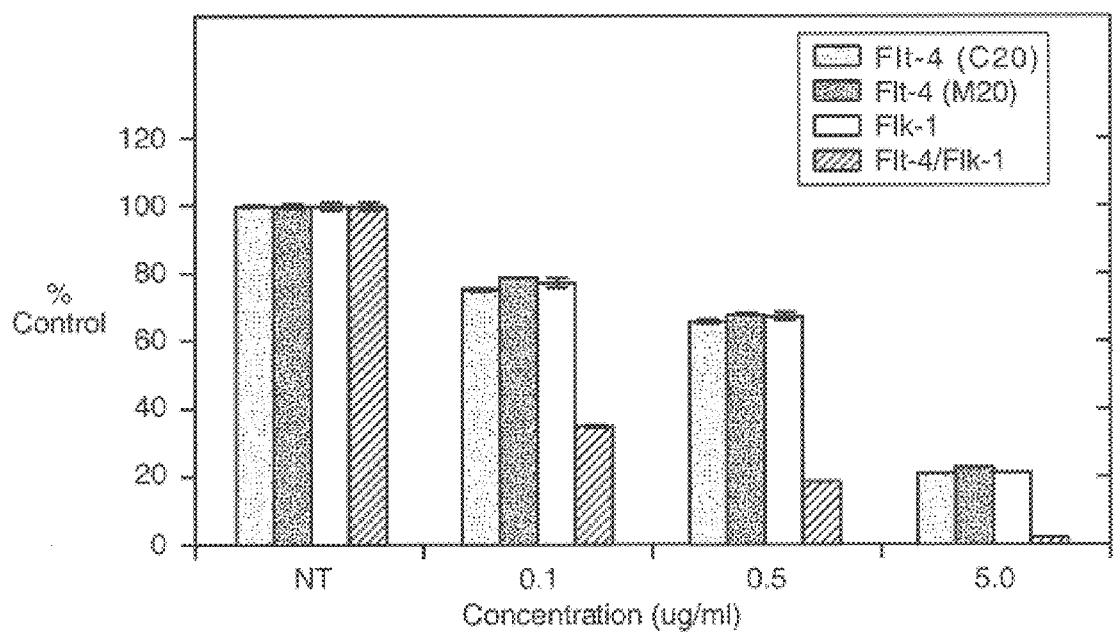
FIG._11A

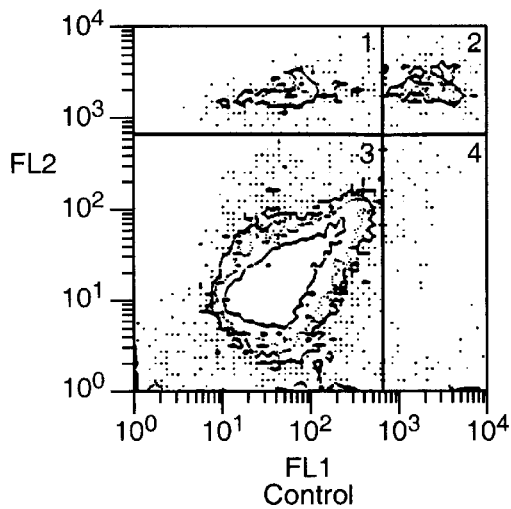
FIG._11B
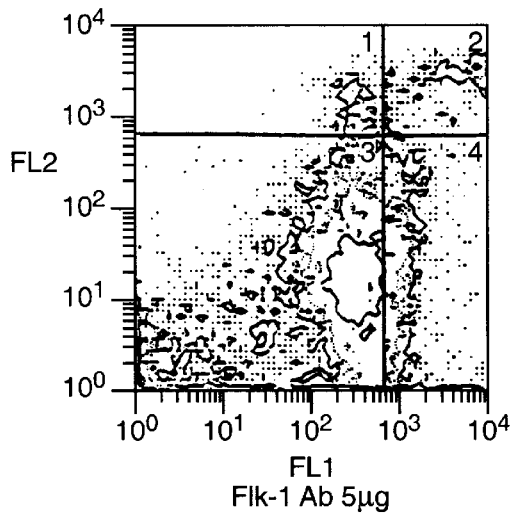
FIG._11C
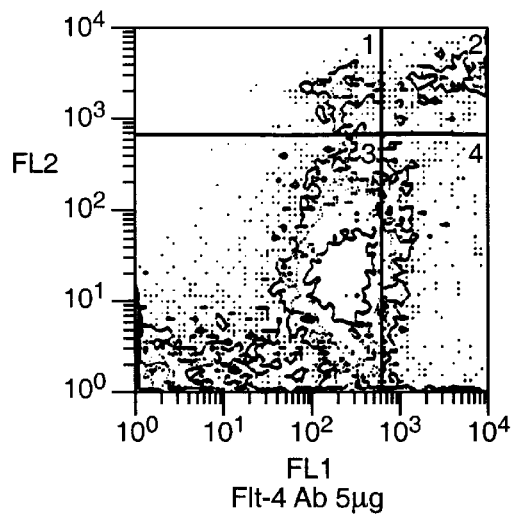
FIG._11D
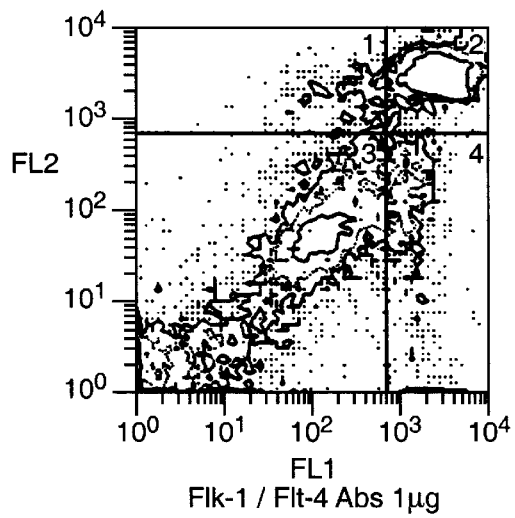
FIG._11E
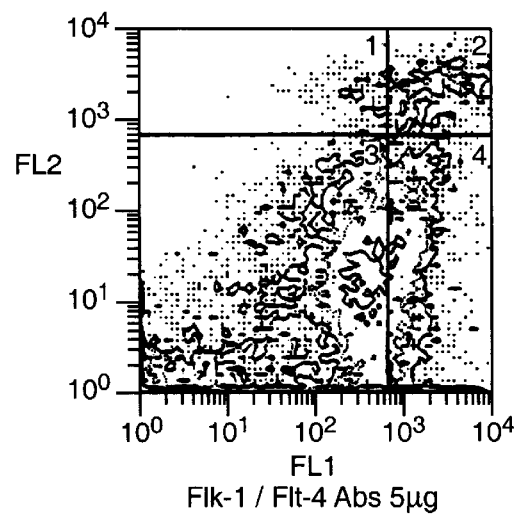
FIG._11F

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Antisense oligonucleotide to a naturally
      occurring sequence

<400> SEQUENCE: 1
agacagcaga aagttcatgg t                                              21

<210> SEQ ID NO 2
<211> LENGTH: 21
<212> TYPE: DNA
<213> ORGANISM: Artificial Sequence
<220> FEATURE:
<223> OTHER INFORMATION: Antisense oligonucleotide to a naturally
      occurring sequence

<400> SEQUENCE: 2
tggcttgaag atgtactcga t                                              21
```

METHOD AND COMPOSITION FOR TREATMENT OF KAPOSI'S SARCOMA

RELATED APPLICATION

This application is a continuation-in part of Ser. No. 60/037,004, filed Jan. 31, 1997.

FIELD OF INVENTION

The invention relates to the pharmacological use of VEGF antagonists antisense oligonucleotides (Veglin-1 (SEQ ID NO. 1) and Veglin-3 (SEQ ID NO. 2)) in a specific disease state. More particularly this invention relates to the use of VEGF inhibitors in the treatment of Kaposi's sarcoma (KS) in patients by administrating to the patients an effective amount of VEGF antagonist which is capable of inhibiting the growth of KS cells in culture. The VEGF agonist may be administered topically, orally or parenterally.

The invention also relates to the use of novel VEGF inhibitor antisense oligonucleotides (Veglin-1 (SEQ ID NO. 1 and Veglin-3 (SEQ ID NO. 2)) in the treatment of other diseases in which vascular proliferation plays a role, such as cancers, proliferative retinal diseases, collagen vascular diseases such as rheumatoid arthritis and lupus erythematosis, psoriasis and pemphigus etc. The invention also includes the use of KS cell lines as a rapid method to screen for compounds that inhibit VEGF effects.

BACKGROUND OF THE INVENTION

Kaposi's sarcoma (KS) is the most common tumor seen in patients with HIV-1 infection (Lifson AR et al. American Journal of Epidemiology 1990, 131:221–231. Reynolds P et al. American Journal of Epidemiology 1993,137:19–30.). KS causes significant morbidity and mortality through involvement of the skin and visceral organs. While the etiologic agent, if any, is unknown, substantial knowledge has been gained regarding the factors regulating the growth of tumor cells (Reynolds et al).

Kaposi's sarcoma most frequently presents as skin lesions (Lifson et al). Mucosal (oral cavity) involvement is the second most common site of disease, occurring on the palate and gums and can cause tooth loss, pain and ulceration. Lymph node involvement is common with KS. However, the precise frequency is not known due to the lack of routine lymph node biopsies.

Visceral involvement occurs frequently, (in nearly 50% of the cases) especially in patients with advanced disease (Laine L et al. Arch Intern Med 1987, 147:1174–1175.). Advanced gastrointestinal (GI) KS can cause enteropathy, diarrhea, bleeding, obstruction and death. Pulmonary involvement is common and significant pulmonary KS occurs in nearly 20% of the cases (Laine L et al. Arch Intern Med 1987, 147-:1174–1175. Gill PS et al. Am J Med 1989, 87:57–61). The symptoms vary from no symptoms to dry cough, exertional dyspnea, hemoptysis and chest pain. Pulmonary function studies may show varying degree of hypoxemia. The overall survival of patients with symptomatic pulmonary KS is less than 6 months (Gill et al).

While the skin, lung, and GI tract are common sites of disease, nearly every organ can be involved with KS, including liver, spleen, pancreas, omentum, heart, pericardium, etc.

Phenotypic studies to define the cell of origin of KS have been performed extensively. KS spindle cells express phenotypic features of mesenchymal cells and share some markers with endothelial cell, vascular smooth muscle cells, and dermal dendrocytes. The markers shared with endothelial cells include lectin binding sites for Ulex Europeaus Agglutinin-1 (UEA-1), CD34, EN-4, and PAL-E. The expression of several factors markers in HUVEC, AIDS-KS cells and trans differentiated HUVEC was confirmed by histochemistry and RT-RCR message analysis for expression of IL-6, IL-8, GM-CSF, TGF-$\beta$ etc.

AIDS-KS spindle cell isolation have allowed the determination of factors secreted by the tumor cells and their effects on the tumor cell itself Both IL-1 $\beta$ and IL-6 are produced by tumor cells. Further, the inhibition of their effects either through blocking their binding to the cognate receptors (IL-1 receptor antagonist, soluble IL-1 receptor) or inhibition of gene expression through antisense olignucleotides (for IL-6) inhibits the growth of tumor cells. More importantly, both IL-1 and IL-6 induce VEGF expression. Thus endogenous production of these factors may in part be responsible for high levels of VEGF production by KS cells.

VEGF was first discovered as a molecule that is a secreted protein with biological effects which include the following. VEGF in vitro induces the growth of endothelial cells and induces migration of endothelial cells. VEGF induces new vessel formation in model systems, such as the chick chorioallantoic membrane and the rat or rabbit cornea avascular zone. VEGF induces permeability of the existing blood vessels, in model systems, such as the mice of guinea pig skin vessels. It was later shown that a number of tumor cells produce VEGF and the secreted protein induces the regional blood vessels to produce more blood vessel network to support the tumor growth and metastasis. In addition inhibition of VEGF function was shown to reduce the growth potential of tumor explants in immunodeficient mice. VEGF expression is increased by hypoxia as noted in the deepest part of the tumor, and by certain cytokines, such as IL-1 and IL-6. VEGF functions through the cognate tyrokinase receptors, Flt-1 and Flk-1/KDR. Flt-1 is an intermediate affinity receptor and Fik-1/KDR is a low affinity receptor. Expression of both receptors results in high affinity binding of the homodimer of VEGF to the target cells. Signal transduction however occurs through Fik-1/KDR only. The expression of VEGF receptors thus is essential for its biological activity and the restricted expression in activated endothelial cells lining the blood vessels.

VEGF is expressed as four different spliced variants. VEGF 165 and VEGF 121 are secreted proteins. Four other members of the VEGF family have been described recently. These include VEGF-B, VEGF-C, VEGF-D, and placental derived growth factor (PIGF). KS cells express all members of the VEGF family, as well as the receptors for VEGF and VEGF-C (Flt-4). PIGF has 47% homology to VEGF and binds to Flt-1 as a homodimer or a heterodimer with VEGF. VEGF-B is a 167 amino acid secreted protein and has 43% and 30% homology with VEGF and PIGF. VEGF-C also called VEGF related protein (VRP) has 32% and 27% homology to VEGF and PIGF. It binds to Flt-4 as a homodimer and to Flk-1/KDR as a VEGF heterodimer.

The hallmark of KS is the aberrant and enhanced proliferation of vascular structures. Various angiogenic factors have been isolated for their ability to enhance endothelial cell proliferation and migration in-vitro. The analysis of AIDS-KS cells have revealed the expression of basic fibroblast growth factor (bGFG) and vascular endothelial cell growth factor (VEGF). The latter is a secreted molecule with capability to induce capillary permeability, a prominent feature of a subset of AIDS-KS. Inhibition of VEGF expression may have therapeutic efficacy in KS. In addition, the isolation of several members of the VEGF family reveals that there is a redundancy and modulation of VEGF function. It is thus conceivable, that the inhibition of VEGF alone may be active as a therapeuric strategy to inhibit tumor growth, while inhibition of several or all members of this family may be more effective.

The treatment of AIDS-related Kaposi's sarcoma is palliative. Localized KS can be managed with local therapy including radiation therapy. Radiation therapy produces local toxicity and has a cumulative dose limiting toxicity. Other options for the cosmetic treatment of localized disease include cryotherapy, photodynamic therapy, intralesional vinblastine, and intralesional sclerosing agents, all of which result in local toxicity of pigmentation which may at times be worse than the lesions itself.

Progressive KS especially with local complications of pain, edema, and ulceration and symptomatic visceral KS, require therapy which will result in rapid response. Systemic cytotoxic chemotherapy is the only treatment modality that produces rapid response. The frequency of response however depends on the agent, dose, and schedule. The response to therapy varies from 25% to over 50%. The most active agents include vinca alkaloids (vincristine, vinblastine), etoposide, anthracyclines and bleomycin. Combination therapies are more active than single agent treatments. However, the majority of cytotoxic agents cannot be administered for a prolonged period of time due to cumulative toxicity. Treatment with cytotoxic chemotherapy is palliative and the nearly all patients relapse within weeks of discontinuation of therapy.

SUMMARY OF THE INVENTION

The current invention discloses methods for treating Kaposi's sarcoma with inhibition of VEGF at therapeutic doses. Specifically, this invention demonstrates that KS can be lessened and that further tumor growth and spread can be blocked with the use of specific VEGF inhibitors, antisense oligonucleotides (Veglin-1 (SEQ ID NO. 1) and Veglin-3 (SEQ ID NO. 2)). This invention also details the parenteral administration of VEGF inhibitors (Veglin-1 (SEQ ID NO. 1) and Veglin-3 (SEQ ID NO. 2 )) encapsulated in liposomes. This invention postulates that other inhibitors of VEGF or VEGF receptors or VEGF binding to the VEGF receptor on the cells such a VEGF antibodies, VEGF receptor (Flk-1/KDR, and Flt-1) antibodies or soluble form of the receptors, which are exemplary but not exclusive, can be used for the treatment of KS. This invention also postulates that the specific VEGF antisense oligonucleotides (Veglin-1 (SEQ ID NO. 1) and Veglin-3 (SEQ ID NO. 2)), claimed here can also be used in a variety of diseases including cancers and precancerous conditions, solid tumors, proliferative retinopathy (diseases of the eye in which proliferation of the blood vessels cause visual loss), proliferative angiopathies of Diabetes Mellitus, collagen vascular diseases, including rheumatoid arthritis and lupus erythematosis, and skin diseases such as psoriasis and pemphigus. This invention also discloses the method of discovering new inhibitors of VEGF using KS cell lines since no other tumor cell line produces and uses VEGF for its own growth.

BRIEF DESCRIPTION OF FIGURES

FIGS. 1A–1C show that KS cells produce VEGF protein at high levels when compared to other cell types such as fibroblasts, endothelial cells, and vascular smooth muscle cells. Equal number of cells were grown in 25 cm2 flasks and the supernatants were collected after 24 hr, and the VEGF levels were measured by ELISA.

FIG. 2 illustrates expression of all members of the VEGF family by KS cell lines, whereas no expression is observed in B cell and fibroblast cell lines.

FIGS. 3A–3B show that KS cells lines and primary KS tumors express both VEGF receptors (Flk-1/KDR and Flt-1). Several other cell lines including T-cell lines, B-cell lines and fibroblast cell lines were tested and none of which had any evidence of VEGF receptor expression. Normal human endothelial cells as expected served as positive controls. KS cells and control cells were grown in 75 cm 2 flasks until near confluence. Total cellular RNA was solubilized in guanidium thiocyanate and cDNA synthesized. Using a specific primer pair for each of the two VEGF receptors, the mRNA transcripts were amplified and the product was resolved on agarose gel.

FIG. 4 illustrates that various KS cell lines also express the VEGF-C receptor (Flt-4).

FIGS. 5A–5B show that many of the tumor types, including colon (HT-29), breast (ZR-75), pancreas (panc), ovarian (ova-3), and melanoma (A-375), express VEGF and VEGF-C (FIG. 5A), while expression of the other VGEF family members is heterogeneous (FIG. 5B).

FIGS. 6A–6F show that VEGF is an autocrine growth factor for KS tumor cells. Antisense oligonucleotides to various coding regions of the human VEGF gene were synthesized and phosphorothioate modified to reduce rate of degradation. Equal number of cells were seeded in 24 well plates. The molar concentration-dependent potency of VEGF antisense oligonucleotides for inhibition of growth of KS cells was examined in the cell proliferation assays after exposure of the cells on day 1 and 2, and cell counts performed on day 3. Viable cell counts were determined by Coulter counter. Each value is the mean+SE of assays performed in triplicate. The controls included scrambled phosphorothioate modified oligonucteotides. In addition, the control experiments included cell lines including T-cell lines, B-cell lines, smooth muscle cells, endothelial cells and fibroblast. Only two antisense oligonucleotides showed inhibition of KS cell lines, while others had no significant effect. These oligonucleotides AS-1 and AS-3 will from hereon will be referred to as Veglin-1 (SEQ ID NO. 1) and Veglin-3 (SEQ ID NO. 2). It is also notable that Veglin-1 (SEQ ID NO. 1) and Veglin-3 (SEQ ID NO. 2) had no significant effect on the growth of various control cell lines such as B cell lines, T cell lines and fibroblast cell lines.

FIGS. 7A–7G illustrate specificity of VEGF antisense oligonucleotides.

FIG. 8 shows that Veglin-1 (SEQ ID NO. 1) and Veglin-3 (SEQ ID NO. 2) are active in vivo to inhibit KS tumor growth. The immunodeficient mice bearing KS explants were treated with Veglin-1 or Veglin-3 or scrambled oligonucleotides, each given intraperitoneally daily for five days beginning one day after the tumor explants. The tumors were then allowed to grow for a total of 14 days. The tumor sizes were measured. The animals were then sacrificed and the tumors were removed and measured again.

FIGS. 9A–9B illustrates the effects of liposomal encapsulation of Veglin-1 (SEQ ID NO. 1) and Veglin-3 (SEQ ID NO. 2). We have shown previously that liposomes deliver higher amounts of the drugs into the KS tumor cells than the free drugs. We thus encapsulated Veglin-1 (SEQ ID NO. 1) and Veglin-3 (SEQ ID NO. 2) in the liposomes and treated the KS cells seeded at equal density in 24 well plates. The cell counts were performed on day 5 and the results are presented as the mean and±SE of assays performed in triplicate. Veglin-1 (SEQ ID NO. 1) and Veglin-3 (SEQ ID NO. 2) induced 50% inhibition of KS cell growth (IC 50) at doses 50 fold lower than required for free Veglin-1 and Veglin-3.

FIGS. 10A–10B describe the effect of VEGF on KS cell survival. VEGF is a survival factor for KS cells and blocking VEGF production with Veglin-1 (SEQ ID NO. 1) or Veglin-3 (SEQ ID NO. 2) causes cell death in KS cell. In addition to the demonstration that VEGF is an autocrine growth factor for KS cells, we wished to determine if VEGF is required for the survival of KS cells. KS cells were seeded at equal density in 75 $cm^2$ flasks, serum starved for 24 hr and treated with either Veglin-1 or Veglin-3 or scrambled otigonucleotides, and the cell death was measured by examining the liberation of small DNA fragments (which represents a specific method of cell death called programmed cell death or apoptosis). The DNA was extracted and size fractionated on the agarose gel.

FIGS. 11A–11F illustrate the effect of Flk-1 and Flt-4 antibodies (separate and in combination) on KS Y1 cell proliferation.

DETAILED DESCRIPTION OF THE INVENTION

The term "response" means a halt in the progression of KS lesions and/or a decrease in tumor size without accompanying unwanted side effects.

The term "partial response" means a complete flattening of more than 50% of the raised lesions lasting for four weeks or more.

The term "pharmacologically acceptable carrier" means any chemical approved for use by the Food and Drug Administration as part of a drug formulation.

The term "therapeutically effective dose" of a VEGF antagonist means an amount calculated to achieve and maintain a therapeutically effective level in the tumor, if applied to the tumor, or in the plasma, if administered systemcally, as to substantially inhibit the proliferation of KS cells. It is preferred that the therapeutic amount be sufficient to inhibit proliferation of more than 50 percent of KS cells in vitro. Of course, the therapeutic dose will vary with the potency of each VEGF antagonist in inhibiting KS cell growth in vitro, and the rate of elimination or metabolism of the VEGF antagonist by the body in the tumor tissue and /or in the plasma.

The term "antagonist" means compounds that prevent the synthesis of the target molecule or bind to the cellular receptor of the target molecule or an agent that blocks the functional of the target molecule.

The term "antisense oligonucleotides" means a sequence of nucleic acids constructed so as to bind to the mRNA of a certain protein and prevent translation by ribosomes into protein.

The terms "sense oligonucleotides", "oligonucleotide fragment" or "polynucleotide fragment", "portion," or "segment" refers to a stretch of nucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "scrambled oligonucleotide" means a sequence of nucleic acid constructed so as to match the nucleic acids content but not the sequence of a specific oligonucleotide.

VEGF is produced by KS cells, VEGF receptors (Flk-1/KDR, Flt-1) are expressed in KS cells and the cell growth is enhanced by VEGF and KS cell survival depends on VEGF. Thus KS is the first tumor type in which VEGF has direct biological effects. In vitro studies have shown that KS cells express VEGF at high levels. In addition, VEGF receptors (Flt-1 and KDR) were shown to be expressed in KS cell lines. Furthermore the addition of VEGF to the KS cells was shown to enhance KS cell growth although it was less dramatic than seen in endothelial cells. These findings for the first time showed that KS cells express functional receptors and that VEGF acts as a growth factor for KS. This is the first demonstration of any tumor cell type to use VEGF for its own growth. The role of VEGF was documented after the VEGF expression was blocked in KS cells with the use of novel antisense oligonucleotides (Veglin-1 (SEQ ID NO. 1) and Veglin-3 (SEQ ID NO. 2)). These findings indicated that under the normal conditions, the VEGF produced by the tumor cells binds with the VEGF receptors and keeps the cells proliferating. In addition, it was shown that the blockage of VEGF production by the novel antisense oligonucleotides (Veglin-1 (SEQ ID NO. 1) and Veglin-3 (SEQ ID NO. 2)) lead to the KS cell death, indicating that VEGF not only is required for the growth of the tumor cells, but for the cell survival. These findings were then confirmed in the primary tumor tissues showing that VEGF and VEGF receptors are expressed in the tumor, while the normal adjoining tissue biopsies did not show expression of either VEGF or VEGF receptors. These findings were reduced to practice by performing experiments in vivo in the mouse model. KS tumors implanted in the immunodeficient mice were treated only for a short period and the growth of the tumor was studied for several additional days. Novel antisense oligonucleotides (Veglin-1 (SEQ ID NO. 1) and Veglin-3 (SEQ ID NO. 2)) blocked the growth of the tumor.

As described herein, the present invention provides a number of oligonucleotide sequences that specifically inhibit the synthesis of VEGF protein and thus are able to block KS tumor growth. In a preferred embodiment these oligonucleotides include Veglin-1 which has the following sequence SEQ ID NO. 1 5'-AGA CAG CAG AAA GTT CAT GGT-3' and Veglin-3 which has the following sequence SEQ ID NO. 2 5'-TGG CTT GAA GAT GTA CTC GAT-3'.

With the published nucleic acid sequences and this disclosure provided, those of skill in the art will be able to identify, without undue experimentation, other antisense nucleic acid sequences that inhibit VEGF expression. For example, other sequences targeted specifically to human VEGF nucleic acid can be selected based on their ability to be cleaved by RNAse H. The oligonucleotides of the invention are composed of ribonucleotides, deoxyribonucleotides, or a combination of both, with the 5' end of one nucleotide and the 3' end of another nucleotide being covalently linked. These oligonucleotides are at least 14 nucleotides in length, but are preferably 15 to 28 nucleotides long, with 15 to 25 mers being the most common.

These oligonucleotides can be prepared by the art recognized methods such as phosphoramidate or H-phosphonate chemistry which can be carried out manually or by an automated synthesizer as described in Uhlmann et al. (Chem. Rev. (1990) 90:534–583).

The oligonucleotides of the invention may also be modified in a number of ways without compromising their ability to hybridize to VEGF mRNA. For example, the oligonucleotides may contain other than phosphodiester internucleotide linkages between the 5' end of one nucleotide and the 3' end of another nucleotide in which the 5' nucleotide phosphodiester linkage has been replaced with any number of chemical groups. Examples of such chemical groups include alkylphosphonates, phosphorothioates, phosphorodithioates, alkylphosphonothioates, phosphoramidates, phosphate esters, carbamates, acetamidate, carboxymethyl esters, carbonates, and phosphate triesters. Oligonucleotides with these linkages can be prepared according to known methods (see, e.g., Uhlmann et al. (1990) Chem. Rev. 90:543–583).

The preparation of these and other modified oligonucleotides is well known in the art (reviewed in Agrawal et al. (1992) Trends Biotechnol. 10:152–158). For example, nucleotides can be covalently linked using art-recognized techniques such as phosphoramidate, H-phosphonate chemistry, or methylphosphoramidate chemistry (see, e.g., Uhlmann et al. (1990) Chem. Rev. 90:543–584; Agrawal et al. (1987) Tetrahedron. Lett. 28:(31):3539–3542); Caruthers et al. (1987) Meth. Enzymol, 154:287–313; U.S. Pat. No. 5,149,798). Oligomeric phosphorothioate analogs can be prepared using methods well known in the field such as methoxyphosphoramidite (see,e.g., Agrawal et al. (1988) Proc. Natl. Acad. Sci. (USA) 85:7079–7083) or H-phosphonate (see, e.g., Froehler (1986) Tetrahedron Lett. 27:5575–5578) chemistry. The synthetic methods described in Bergot et al. (J. Chromatog. (1992) 559:35–42) can also be used.

The present invention also provides polyclonal and/or monoclonal antibodies, including fragments and immunologic binding equivalents thereof, which are capable of specifically binding to the polynucleotide sequences of the specified gene (and fragments thereof) as well as the corresponding gene products (and fragments thereof). In general, techniques for preparing polyclonal and monoclonal antibodies as well as hybridomas capable of producing the desired antibody are well known in the art (Campbell, 1984; Kohler and Milstein, 1975). These include, e.g., the trioma technique and the human B-cell hybridoma technique (Kozbor, 1983; Cole, 1985).

Any animal (mouse, rabbit, etc.) that is known to produce antibodies can be immunized with the immunogenic composition. Methods for immunization are well known in the art and include subcutaneous or intraperitoneal injection of the immunogen. One skilled in the art will recognize that the amount of the protein encoded by the nucleic acids of the present invention used for immunization will vary based on the animal which is immunized, the antigenicity of the immunogen, and the site of injection. The protein which is used as an immunogen may be modified or administered in an adjuvant to increase its antigenicity. Methods of increasing antigenicity are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify hybridoma cells that produce an antibody with the desired characteristics. These include screening the hybridomas with an enzyme-linked immunosorbent assay (ELISA), western blot analysis, or radioimmunoassay (RIA) (Lutz, 1988). Hybridomas secreting the desired antibodies are cloned and the immunoglobulin class and subclass may be determined using procedures known in the art (Campbell, 1984).

Techniques described for the production of single chain antibodies (U.S. Pat. No. 4,946,778) can be adapted to produce single chain antibodies to the proteins of the present invention. For polyclonal antibodies, antibody-containing antisera is isolated from an immunized animal and is screened for the presence of antibodies with the desired specificity using one of the above described procedures.

In the present invention, the above-described antibodies are used in a labeled form to permit detection. Antibodies can be labeled, e.g., through the use of radioisotopes, affinity labels (such as biotin, avidin, etc.), enzymatic labels (such as horseradish peroxidase, alkaline phosphatase, etc.) fluorescent labels (such as fluorescein or rhodamine, etc.), paramagnetic atoms, etc. Procedures for accomplishing such labeling are well-known in the art, e.g., see Sternberger, 1970; Bayer, 1979; Engval, 1972; Goding, 1976. The labeled antibodies of the present invention can then be used for in vitro, in vivo, and in situ assays to identify the cells or tissues in which a fragment of the polypeptide of interest is expressed. Preferred immunoassays are the various types of ELISAs and RIAs known in the art (Garvey, 1977). The antibodies themselves may also be used directly in therapies or other diagnostics.

The synthetic oligonucleotides of the invention may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art.

The pharmaceutical composition of the invention may also contain other active factors and/or agents which enhance inhibition of VEGF expression or which will reduce neovascularization. For example, combinations of synthetic oligonucleotides, each of which is directed to different regions of the VEGF mRNA, may be used in the pharmaceutical compositions of the invention. The pharmaceutical composition of the invention may further contain nucleotide analogs such as azidothymidine, dideoxycytidine, dideoxyinosine, and the like. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-VEGF or anti-neovascularization factor and/or agent to minimize side effects of the anti-VEGF factor and/or agent.

The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in Szoka et al., Ann. Rev. Biophys. Bioeng. 9:467 (1980), U.S. Pat. Nos. 4,235,871, 4,501,728, 4,837,028, the text Liposomes, Marc J. Ostro, ed., Chapter 1, Marcel Dekker, Inc., New York (1983), and Hope, et al., Chem. Phys. Lip. 40:89 (1986), all of which are incorporated herein by reference.

The pharmaceutical composition of the invention may further include compounds such as cyclodextrins and the like which enhance delivery of oligonucleotides into cells, as described by Zhao et al. (in press), or slow release polymers.

The following examples illustrate the manner in which the invention can be practiced. It is understood, however, that the examples are for the purpose of illustration and the invention is not to be regarded as limited to any of the specific materials or conditions therein.

EXAMPLES

Materials and Methods

Antibodies used include p-130 and Tie-1 antibodies. Antibody p130 is an affinity purified rabbit polyclonal antibody raised against a peptide corresponding to amino acids 1120–1139 mapping at the carboxy terminus of p130 of human origin. Antibody Tie-1 is an affinity-purified rabbit polyclonal antibody raised against a peptide corresponding to amio acids 1121–1138 mapping at the carboxy terminus of the precursor form of Tie-1 of human origin.

Isolation of KS cells. AIDS-KS-derived spindle cell strains were isolated from primary tumor tissues as described previously (Nakamura et al. 1988). Cells were cultured continuously in 75 cm$^2$ flasks coated with 1.5% gelatin, in KS medium consisting of the following: RPMI 1640 (Life Technologies), 100 U/ml penicillin, 100 $\mu$g/ml streptomycin, 2 mM glutamine, essential and nonessential amino acids, 10% fetal bovine serum (FBS, Life Technologies), and 1% Nutridoma-HU (Boehringer Mannheim). The primary isolates were characterized to determine their phenotype using immunofluorescent assay. The markers expressed include endothelial cell markers; UEA-1 binding sites, EN-4, PALE; smooth muscle cell specific markers including vascular smooth muscle cell specific alpha actin; macrophage specific marker including CD14. Neoplastic cell line KSY-1 is propagated similarly and has similar phenotype.

Example 1

Expression of VEGF and VEGF-C Receptors by KS Cells

In vitro studies showed that KS cells express all members of the VEGF family at high levels. Expression of Flt-1 and KDR mRNA in KS cell line (KSY1), HUVE, normal skin and KS tumor tissue from an HIV+ patient, T1 (fibroblast), 23-1 (B-lymphoma) and HUT-78 (T cell lymphoma). Equal amounts of RNA were reverse transcribed to generate cDNA. cDNA was either subjected to Flt-1 or KDR specific PCR amplification (500 and 700 bp products respectively) using paired primers and cDNA from all samples were subjected to β-actin specific PCR amplification (548 bp product).

Example 2

Expression of VEGF mRNA and Production of VEGF Protein by KS Cells

Expression of VEGF mRNA was analyzed in several AIDS-KS cell lines. Preferably, 15 $\mu$g of total RNA from (I) KSC10, KSC29, KSC13, KSC59 and KSY1 (FIG. 1A) or (ii) KSC10, HUVEC and AoSM (FIG. 1B) were electrophoresed, blotted and hybridized to the human VEGF cDNA and β-actin probe. Supernatants from equal numbers of cells from KSY1, AoSM, HUVEC and T1 were collected after 48 hours-and analyzed for VEGF protein by ELISA (FIG. 1C).

Example 3

Effect of VEGF Antisense Oligonucleotides on KS Cell Growth

[A] KS cells were treated with VEGF antisense AS-1 (Veglin-1), AS-3 (Veglin-3), and the scrambled oligonucleotides at concentrations ranging from 1 to 10 mM. Cell proliferation was measured on day 5. Data represent the mean±standard deviation of two separate experiments performed in quadruplicate. [B] Effect of rhVEGF on the growth of KS and HUVEC cells. Cells were seeded at 1×10$^4$ cells per well in 24 plates and treated with rhVEGF (1 to 10 ng/mi) for 48 hours. Cell counts were performed and the results represent the mean±SD of an experiment performed in quadruplicate. [C] rhVEGF abrogates the effect of VEGF antisense on AIDS-KS cell growth. KS cells were seeded at a density of 1×10$^4$ cells per well in 24 well plates. Cells were treated with 1 and 10 mM of AS-3 (Veglin-3) alone or with rhVEGF(10 ng/ml) on day 1 and day 2. Cell proliferation was measured after 72 hours. The data represent the mean±standard deviation of two experiments performed in quadruplicate. As shown by the results summarized in FIGS. 6A–6F, incubation of AIDS-KS cells for 3 days with antisense oligonucleotides results in a dose dependent inhibition of KS cell growth, as measured by cell count. In contrast, the sense oligonucleotides did not result in significant inhibition of KS cell growth. These findings indicate that VEGF is an autocrine growth factor for KS cells.

Example 4

Specificity of VEGF Antisense Oligonucleotides

Cells were seeded at equal density and treated with either Veglin-1 or Veglin-3, or scrambled oligonucleotides, followed by a cell count and extraction of total cellular RNA. Total RNA was isolated from AIDS-KS cells treated with various concentrations of AS-1/Veglin-1 [FIG. 7A], AS-3/Veglin-3 [FIG. 7B] and S [FIG. 7C]. Total RNA was reverse transcribed to generate cDNA. PCR was carried out for VEGF and β-actin. FIGS. 7A–7C show PCR products of 535 and 403 bp corresponding to VEGF,2, and VEGF,6S mRNA species of VEGF. FIGS. 7D–7F show the 548 bp PCR product of β-actin. NT=No treatment; M=Molecular size marker, 25–41 and 18–33 represent the number of PCR cycles. FIG. 7G illustrates that these VEGF oligonucleotides inhibit the production of VEGF protein in KS cells. The supernatants of KS cells treated with AS3/Veglin-3 and scrambled VEGF antisense oligonucleotide were also collected at 48 hr and VEGF protein was quantitated by ELISA. The results represent the mean±standard deviation of two separate experiments done in duplicate.

Example 5

Inhibition of KS Tumor Growth by VEGF Oligonucleotides

The effect of tumor growth by VEGF antisense oligonucleotide was also studied in nude mice. KS-Y1 (ceE7tE) were inoculated subcutaneously in the lower back of Balb/C/Nu+/NU+ athymic mice. AS-1/Veglin-3, AS-3/Veglin-3, Scrambled (S) VEGF oligonucleotides and diluent (PBS) were injected intra-peritoneally daily for five days (day 2 to 6). Mice were sacrificed on day 14 and tumor size was measured. Data represent the mean±standard deviation of 10 mice in each group. FIG. 8 illustrates the drastic reduction in tumor growth that as a result of treatment with AS-1 or AS-3.

Example 6

Liposomal Encapsulation of VEGF Antisense Oligonucleotides

KS cells were treated with oligonucleotides encapsulated in neutral liposomes at various concentrations on day 1 and day 2 and the cell count was performed on day 3. Cell proliferation was measured after 72 hours (FIG. 9B). The data represent the mean±standard deviation of two experiments performed in quadruplicate. Over 50% reduction in the cell growth was observed at concentration 50 fold below that required for free oligonucleotides. Furthermore scrambled oligonucleotides at the same concentrations had no inhibitory effects (FIG. 9A).

Example 7
Effect of VEGF on KS Cell Survival

In addition, the effect of antisense oligonucleotides on the KS cells survival was studied. KS cells were treated with various concentrations of oligonucleotides. The DNA was extracted and separated on agarose gel. As illustrated in FIG. 10A antisense oligonucleotides at concentrations of 1 $\mu$M and above showed evidence of cell death through the mechanism of programmed cell death, also called apoptosis. Scrambled oligonucleotides however had no effect at concentrations of up to 10 $\mu$M (FIG. 10B).

Example 8
Effect of Flk-1/KDR and Flt-4 Antibodies on KS Cell Growth

FIGS. 11A–11F illustrate that Flk-1/KDR and Flt-4 antibodies inhibited KS cell growth in a dose dependent manner. An increasing effect was observed when they were administered in combination. A similar effect was observed on the receptors, i.e. antibodies to Flk-1 and Flt-1 induced apoptosis in a dose dependent manner, with an additive effect when both were combined. In contrast, antibodies to another endothelial cell receptor tyrosine kinase which is also expressed on KS cells had no effect.

REFERENCES

Agrawal et al. (1992) Trends Biotechnol. 10:152–158.
Agrawal et al. (1987) Tetrahedron. Lett. 28:(31):3539–3542)
Caruthers et al. (1987) Meth. Enzymol, 154:287–313
Agrawal et al. (1988) Proc. Natl. Acad. Sci. (USA) 85:7079–7083
Froehler (1986) Tetrahedron Lett. 27:5575–5578
Bergot et al. (J. Chromatog. (1992) 559:35–42)
Bayer, E. A. et al. (1979) *Meth. Enzym.* 62:308.
Kohler, G. and Milstein, C. (1975) *Nature* 256:495–497.
Kozbor, D. et al. (1983) *Immunology Today* 4:72.
Lutz et al.(1988) *Exp. Cell Research* 175:109–124
Sternberger, L. A. et al. (1970) *J. Histochem. Cytochem.* 18:315.
Garvey, J. S. et al. (1977) *Methods in Immunology*, 3rd ed., W. A. Benjamin, Inc., Reading, Mass.
Goding, J. W. (1976) *J. Immunol. Meth.* 13:215.
Engval, E. et al. (1972) *Immunol.* 109:129.
Campbell, A. M. (1984) *Monoclonal Antibodies Technology: Laboratory Techniques in Biochemistry and Molecular Biology*, Elsevier Science Publishers, Amsterdam, The Netherlands.
Cole et al. (1985) in *Monoclonal Antibodies and Cancer Therapy*, Alan R. Liss, Inc., pp. 77–96.
Lifson A R, Darrow W W, Hessol N A, O'Malley P M, Bamhart J L. Jaffe H W, and Rutherford G W. Kaposi's sarcoma in a cohort of homosexual and bisexual men. American Journal of Epidemiology 1990,131:221–231.
Reynolds P, Saunders L D, Layefsky M E, and Lemp G F. The spectrum of acquired immunodeficiency syndrome (AIDS)-associated malignancies in San Francisco, 1980–87. American Journal of Epidemiology 1993, 137:19–30
Laine L, Politoske E J, Gill P S. Protein-losing enteropathy in acquired immunodeficiency syndrome due to the intestinal Kaposi's sarcoma. Arch Intern Med 1987.147:1174–1175.
Gill P S, Akil B, Rarick M, Colletti P, et al. Pulmonary Kaposi's sarcoma: Clinical findings and results of therapy. Am J Med 1989, 87:57–61.
Russell Jones R, Spaull J, Spry C, Wilson Jones E. Histogenesis of Kaposi's sarcoma in patients with and without acquired immunodeficiency syndrome. J Clin Pathol 1986. 39:742–749.
Weich H A, Salahuddin S Z, Gill P S, Nakamura S, Gallo R, Folkmann J. AIDS associated Kaposi's-derived cells in long-term culture express and synthesize smooth muscle alpha-actin. 1992,139:1251–1258.
Nickoloff B J, Griffith C E M. The spindle-shaped cells in cutaneous Kaposi's sarcoma. Histologic simulators include factor Xlllz dermal dendrocytes. Am J Pathol 1989, 135:793–800.
Miles S A, Rezai A R, Salazar-Gonzales J F, et al. AIDS-Kaposi's sarcoma derived cells produce and respond to interleukin-6. Proc Natl Acad Sci USA 1990, 87:4068.
Louie S, Cai J, Law R et al. The effect of interleukin-1 and IL-1 RA in AIDS-KS. J AIDS. 1995
Nair B C, Devico A L, Nakamura S, et al. Identification of a major growth factor for AIDS-Kaposi's sarcoma cell as Oncostatin-M. Science 1992, 255:1430–1432.
Vogel J, Hinrichs S H, Reynolds R K, et al. The HIV tat gene induces dermal lesions resembling Kaposi's sarcoma in transgenic mice. Nature 335:606–611, 1988.
Ensoli B, S. N, Salahuddin S Z, et al. AIDS-Kaposi's sarcoma-derived cells express cytokines with autocrine and paracrine growth effects. Science 1989, 94.n 223–226.
Barillari G, Buonaguro L, Fiorelli V. et al. Effect of cytokines from activated immune cells on vascular cell growth and HIV-1 gene expression. J Immunol 1992, 149:3727–3734.
Weindel K, Mamme D, Welch H A: AIDS-associated Kaposi's sarcoma cells in culture express vascular endothelial growth factor. Biochem. Biophys. Res. Commun. 1992, 183:1167–1174.
Chak L Y, Gill P S, Levine A M, Meyer P R, Anselmo J A, Petrovich Z. Radiation therapy for Acquired Immunodeficiency Syndrome related Kaposi's sarcoma. J Clin Oncol 1988, 62:735–739.
Shweitzer V G, Visscher D. Photodynamic therapy for treatment of AIDS-related oral Kaposi's sarcoma otolaryngol. Head Neck Surg 1990, 102:639–649.
Krown S E, Real F X, Cunningham-Rundles S, et al. Preliminary observations on the effect of recombinant leukocyte A interferon in homosexual men with Kaposi's sarcoma. N. Engl. J. Med. 1983, 308:1071–1076.
Lane H C, Feinberg J, Davey V, et al. Anti-retroviral effects of interferon-a in AIDS associated KaDosi's sarcoma. Lancet 1988, 2:1218–1222.
Volbering P A, Abrams D 1, Conant M et al. Vinblastine therapy for Kaposi's sarcoma in acquired immunodeficiency syndrome. Ann Int Med 1985,103:335–338.

Mintzer D, Real F X, Jovino L et al. Treatment of Kaposi's sarcoma and thrombocytopenia with vincristine in patients with the acquired immunodeficiency syndrome. Ann Intem Med 1985, 102:200–202.

Laubenstein L J, Krigel R L, Odajnk C M et al. Treatment of epidemic Kaposi's sarcoma with etoposide or a combination of doxorubicin, bleomycin, and vinblastine. J Clin Oncol 1984, 2:1115–1120.

Lassoned S C, Claurel J P, Katlama C, et al. Treatment of acquired immunodeficiency syndrome related Kaposi's sarcoma with bloemycin as a single agent. Cancer 1990, 66; 189 1869–1872.

Gill P S, Rarick M U, McCutchan J A, et al. Systemic treatment of AIDS-related Kaposi's sarcoma. Results of a randomized trial. Am J of Med 1991,19:427–433

Gelman E P, Longo D L, Lane H L, et al. Combination chemotherapy of disseminated Kaposi's sarcoma in patients with the acquired immunodeficiency syndrome. Am J Med 1987, 82:456–459.

Gill P S, Rarick M U, Bernstein-Singer, Harb M, Espina B, Shaw V, Levine A M. Treatment of advanced Kaposi's sarcoma using a combination of Bleomycin and Vincristine. Am J Clin Oncol 1990,13(4):315–319.

Gill P S, Espina B M, Cabriales S, et al. A phase 1/11 clinical and pharmacokinetic evaluation of liposomal daunorubicin (Daunoxome) in the treatment of advanced AIDS-related Kaposi's sarcoma.

Uhlmann et al. (Chem. Rev. (1990) 90:534–583).

2. The composition of claim 1, wherein the antisense oligonucleotide is 5'-AGA CAG CAG AAA GTT CAT GGT-3' (SEQ ID NO 1).

3. The composition of claim 1, wherein the antisense oligonucleotide is 5'-TGG CTT GAA GAT GTA CTC GAT-3' (SEQ ID NO. 2).

4. The composition of claim 1, wherein the antisense oligonucleotide contains one or more phosphorothioate moieties.

5. The composition of claim 2, wherein the antisense oligonucleotide contains one or more phosphorothioate moieties.

6. The composition of claim 3, wherein the antisense oligonucleotide contains one or more phosphorothioate moieties.

7. A VEGF antisense oligonucleotide, wherein the VEGF antisense oligonucleotide is selected from the group consisting of 5'-AGA CAG CAG AAA GTT CAT GGT-3' (SEQ ID NO 1) or 5'-TGG CTT GAA GAT GTA CTC GAT-3' (SEQ ID NO 2).

8. The VEGF antisense oligonucleotide of claim 7, wherein the VEGF antisense oligonucleotide is 5'-AGA CAG CAG AAA GTT CAT GGT-3' (SEQ ID NO 1).

9. The VEGF antisense oligonucleotide of claim 7, wherein the VEGF antisense oligonucleotide is 5'-TGG CTT GAA GAT GTA CTC GAT-3' (SEQ ID NO 2).

10. The VEGF antisense oligonucleotide of claim 7, wherein the antisense oligonucleotide contains one or more phosphorothioate moieties.

What is claimed:

1. A composition, which comprises one or more VEGF antisense oligonucleotides and wherein the one or more antisense oligonucleotides are selected from the group consisting of 5'-AGA CAG CAG AAA GTT CAT GGT-3' (SEQ ID NO 1) or 5'-TGG CTT GAA GAT GTA CTC GAT-3' (SEQ ID NO. 2).

11. The VEGF antisense oligonucleotide of claim 8, wherein the antisense oligonucleotide contains one or more phosphorothioate moieties.

12. The VEGF antisense oligonucleotide of claim 9, wherein the antisense oligonucleotide contains one or more phosphorothioate moieties.

* * * * *